United States Patent [19]

Umezawa et al.

[11] Patent Number: 5,034,517
[45] Date of Patent: Jul. 23, 1991

[54] PROCESS FOR PRODUCING 2,6-DIDEOXY-2-FLUORO-L-TALOPYRANOSE

[75] Inventors: Hamao Umezawa; Sumio Umezawa, both of Tokyo; Tsutomu Tsuchiya, Yokohama; Tomio Takeuchi, Tokyo; Yasushi Takagi, Yokohama, all of Japan

[73] Assignee: Zaidan Hojin Biseibutsu Kagaku Kenkyu Kai, Tokyo, Japan

[21] Appl. No.: 488,871

[22] Filed: Mar. 6, 1990

Related U.S. Application Data

[62] Division of Ser. No. 5,589, Jan. 21, 1987, abandoned.

[30] Foreign Application Priority Data

Jan. 22, 1986 [JP] Japan .................................. 61-9893

[51] Int. Cl.$^5$ ............................................. C07H 1/00
[52] U.S. Cl. ..................... 536/18.5; 536/4.1; 536/6.4
[58] Field of Search ............. 536/18.4, 1.1, 4.1, 536/6.4, 18.5

[56] References Cited

FOREIGN PATENT DOCUMENTS

0181295 10/1984 Japan .................................. 536/18.4

OTHER PUBLICATIONS

Morrison et al., Organic Chemistry, 3rd ed. (1979), pp. 529, 564 and 636.

*Primary Examiner*—Elli Peselev
*Attorney, Agent, or Firm*—Larson and Taylor

[57] ABSTRACT

2,6-Dideoxy-2-fluoro-L-talopyranose and 1-substituted derivatives thereof, including methyl 2,6-dideoxy-2-fluoro-L-talopyranoside and 3,4-di-O-protected-2,6-dideoxy-2-fluoro-L-talopyranosyl halides, are now provided and these new compounds are useful as intermediates for use in the synthesis of new compounds having antitumor activity, especially 7-O-(2,6-dideoxy-2-fluoro-α-L-talopyranosyl) daunomycinone or -adriamycinone. 2,6-Dideoxy-2-fluoro-L-talopyranose shows antibacterial activity. 2,6-Dideoxy-fluoro-L-talopyranose and the 1-substituted derivatives thereof may be produced by a multi-stage process starting from L-fucose.

1 Claim, No Drawings

PROCESS FOR PRODUCING 2,6-DIDEOXY-2-FLUORO-L-TALOPYRANOSE

This is a division of application Ser. No. 07/005,589 filed Jan. 21, 1987 now abandoned.

SUMMARY OF THE INVENTION

This invention relates to 2,6-dideoxy-2-fluoro-L-talopyranose and 1-substituted derivatives thereof which are each a new compound useful as an intermediate product in the synthesis of 7-O-(2,6-dideoxy-2-fluoro-α-L-talopyranosyl)daunomycinone and 7-O-(2,6-dideoxy-2-fluoro-α-L-talopyranosyl)adriamycinone, new compounds having antitumor activity. This invention also relates to processes for the production of 2,6-dideoxy-2-fluoro-L-talopyranose and derivatives thereof. 2,6-Dideoxy-2-fluoro-L-talopyranose itself shows antibacterial activity.

BACKGROUND OF THE INVENTION

Known examples of the antibiotics of anthracycline type include daunomycin (daunorubicin; U.S. Pat. No. 3,616,242) and adriamycin (doxorubicin; U.S. Pat. No. 3,590,028), which both may be obtained from the culture broth of a microorganism of actinomycetes. These two compounds exhibit a wide range of antitumor spectra against a variety of experimental tumors and have been used as a chemotherapeutic agent in the clinic practice. Daunomycin and adriamycin are the compound of the general formula

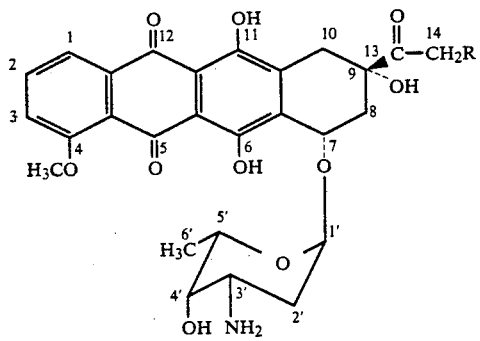

(a)

wherein R is a hydrogen atom or a hydroxyl group. Daunomycin (the compound of the formula (a) above where R is the hydrogen atom) and adriamycin (the compound of the formula (a) where R is the hydroxyl group) can show a fairly high antitumor activity against various kinds of tumors. However, these two compounds are not necessarily an antitumor agent which are completely satisfactory. Thus, daunomycin and adriamycin have been shown to exhibit wide antitumor spectra against the experimental tumors and also have widely been used as a valuable agent for the therapeutic treatment of tumors in the clinic practice. On the other hand, it is known that daunomycin and adriamycin can bring about heavy adverse side-effects that they can cause cardiac toxicity and a decrease in the number of leukocytes and falling-off of the hair in the patients who received the administration of these agents. It is reported that the glycoside linkage between the daunosaminyl group of the formula and the hydroxyl group at the 7-position of daunomycinone or adriamycinone is likely to be broken in vivo by the hydrolysis, and that the moiety of the aglycon as formed by the in vivo hydrolysis, namely the daunomycinone or adriamycinone shows a higher cardiac toxicity than the daunomycin or adriamycin itself.

In the past, therefore, some researches were already made in an attempt to provide new daunomycinrelated compounds which possess a higher anticancer activity and a lower toxicity than daunomycin and adriamycin. For instance, studies for discovering and producing new daumonycin-analogous compounds by fermentative methods, semi-synthetic methods, total synthetic methods or enzymatical conversion methods were conducted. Such particular compounds previously proposed include, for example, aclacinomycins A and B (F. Arcoamone "Topics in Antibiotic Chemistry" Vol. 2, pp. 102–279, published from Elis Horwood Limited, U.S.A.; and U.S. Pat. No. 3,988,315), 4′-O-tetrahydropyranyladriamycin (West Germany Patent No. 2,831,579 and Japanese patent publication No. 47194/81) and N-mono-benzyl- or N-di-benzyl-adriamycin (U.S. Pat. No. 4,177,264).

Further, the specification of U.S. Pat. No. 4,427,664 of Horton et al describes a chemical structure of compounds represented by the general formula

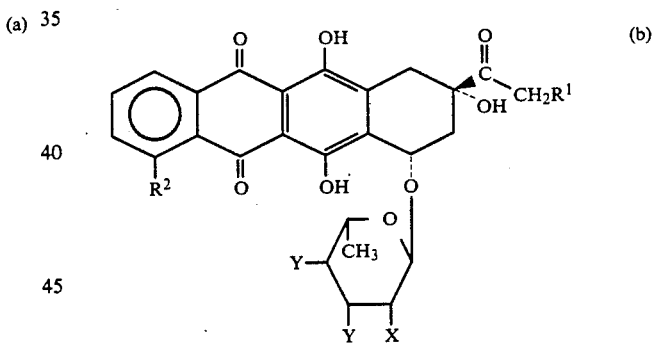

(b)

wherein $R^1$ is a hydrogen atom and $R^2$ is a methoxy group; or $R^1$ is a hydroxyl group and $R^2$ is a methoxy group; or $R^1$ and $R^2$ are each a hydrogen atom; or $R^1$ is a hydrogen and $R^2$ is a hydroxyl group, and X is an iodine, chlorine, bromine or fluorine atom and Y is a hydroxyl group or acetoxy group, and which compounds are of such structure that an aglycon selected from the group consisting of daunomycinone, desmethoxydaunomycinone, adriamycinone and carminomycinone is linked through the oxygen atom at the 7-position thereof to the 1′-position of a sugar of a 2′-halo-α-L-hexopyranose of the α-L-manno type or α-L-talo type. The method of producing a compound of the above formula (b) which is described in the specification of U.S. Pat. No. 4,427,664 is the method wherein an aglycon such as daunomycinone and a glycal, for example, 3,4-di-O-acetyl-L-rhamnal or 3,4-di-O-acetyl-L-fucal, which corresponds to the sugar to be linked to said aglycon are dissolved together in substantially equimolar proportions in a mixture of aprotic organic solvents consisting of anhydrous acetonitrile and tetrahydrofuran and wherein to the resulting solution is then added an iodination agent such as N-iodosuccinimide together with a solvating agent such as dichloromethane at a low reaction temperature so that the aglycon reacts with the said glycal in such way that the glycal used is linked to the 7-hydroxyl group of the aglycon with accompanying by an alkoxyhalogenation of the glycal. According to this method of Horton et al, it happens as described in the specification of said U.S. Pat. No. 4,427,664, that the halogen atom as possessed by the halogenation agent employed is introduced into the 2'-position of the sugar moiety of the compound of the formula (b) formed as the reaction product, and that for instance, when N-iodosuccinimide is employed as the iodination agent, the iodine atom is introduced into the 2'-position of the sugar moiety of the reaction product as obtained.

The U.S. Pat. No. 4,427,664 specification discloses an Experimental Example in which 3,4-di-O-acetyl-L-rhamnal of the formula

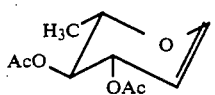

(c)

where Ac denotes an acetyl group here and also hereinafter unless otherwise stated is reacted with daunomycinone and N-iodosuccinimide, with accompanying alkoxyhalogenation of said rhamnal compound, to produce 7-O-(3,4-di-O-acetyl-2,6-dideoxy-2-iodo-α-L-manno-hexopyranosyl)daunomycinone, as well as another Experimental Example in which 3,4-di-O-acetyl-L-fucal of the formula

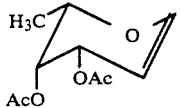

(d)

is reacted with daunomycinone and N-iodosuccinimide with accompanying alkoxyhalogenation of said fucal compound, to produce 7-O-(3,4-di-O-acetyl-2,6-dideoxy-2-iodo-α-L-talo-hexopyranosyl)daunomycinone. However, this U.S. Patent specification does not disclose any further experimental Examples.

In the U.S. Pat. No. 4,427,664 specification, the formula (b) appearing therein refers to that X may broadly be an iodine, bromine, chlorine or fluorine atom, but there is not shown any Experimental Examples in which such a compound of the formula (b) where X is the bromine, chlorine or fluorine atom was virtually synthetized. If the one skilled in the art wishes to synthetize a compound of the above formula (b) where X is the bromine, chlorine or fluorine atom, it is expected that in accordance with the method of producing the compound of the formula (b) taught in the U.S. Pat. No. 4,427,664 specification, he will repeat the procedures of the two Experimental Examples as given in said U.S. patent specification using N-bromosuccinimide, N-chlorosuccinimide or N-fluorosuccinimide as the halogenation agent in place of the N-iodosuccinimide employed by Horton et al. Among the above-mentioned three compounds which are expectedly employable as the halogenation agent in place of the N-iodosuccinimide, a substance which is to be represented by the formula

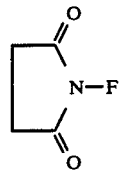

(e)

and which may be termed as N-fluorosuccinimide is unknown by now, because it is not described before in any literatures with respect to any process of preparing it and with respect to the physical and chemical properties of it, as far as we, the present inventors, have searched numerous literatures. Accordingly, it is evidently considered that a compound which may be termed as N-fluorosuccinimide is an actually unknown substance which was never prepared in the past prior to these days.

Besides, it is to be noted that the fluorine element which may be and have usually been considered to belong to the class or family of halogens is possessing an extraordinarily different and higher electric negativity than the other halogen elements, iodine, bromine and chlorine, and also that, as be well known, the fluorine element shows the chemical behaviors very much different from those of the other halogen elements. Accordingly, even when it is assumed that the N-fluorosuccinimide will have been prepared by any chemical process, it is highly probable that the properties of the chemical linkage between the fluorine atom and the succinimide group existing in the N-fluorosuccinimide as an imaginable compound would be very much different from the properties of the other sorts of a halo group linking to the succinimide group, and that such fluoro group is too strongly or too weakly linking to the succinimide group. For these reasons, it is very much hardly conceivable that the N-fluorosuccinimide can act as a fluorination agent to transfer its fluoro group into a second compound and bring about the fluorination of the latter compound. Accordingly, it is not presumable that the N-fluorosuccinimide, even if prepared, can serve especially as the fluorination agent required in the method of producing the compounds of the formula (b) which is described in the U.S. Pat. No. 4,427,664 specification.

In short, the U.S. Pat. No. 4,427,664 specification describes the chemical structure of the compounds of the above formula (b) where X may broadly be a chlorine, bromine, iodine or fluorine atom. Of the compounds which are designated by the above formula (b), the compounds of the formula (b) where X is a chlorine or bromine atom are shown merely with reference to their chemical structure in the U.S. Pat. No. 4,427,664 specification but were actually not synthetized concretely. Nonetheless, it is admittable that N-chlorosuccinimide and N-bromosuccinimide are a chlorination or bromination agent already known and necessary and available as the halogenation agent in the process of producing such compound of the formula (b) where X=chlorine or bromine, according to said U.S. patent of Horton et al, and therefore it is deducible from the descriptions of the U.S. Pat. No. 4,427,664 specification that the production of such compounds of the formula (b) where X=chlorine or bromine and isolation of such compounds as produced are possible theoretically in accordance with the method of Horton et al as disclosed in said U.S. patent specification. In contrast, however, it is evident that the U.S. Pat. No. 4,427,664 specification does not disclose or teach a process for really producing such compound of the formula (b) where X is the fluorine atom, to such extent that the process would be workable by chemical experts in view of the disclosure of the U.S. Pat. No. 4,427,664, firstly, because the N-fluorosuccinimide which is deemed as necessary as the fluorination agent for the production of the compound of the formula (b) where X=fluorine, according to the disclosed method of Horton et al is a substance which is still unknown up to now and is very much suspicious to be able to act successfully as the necessary fluorination agent for the intended purpose, and secondly, because the U.S. Pat. No. 4,427,664 of Horton et al does nowhere teach how to prepare the N-fluorosuccinimide. Hence, it is worthy to say that such compound of the above formula (b) where X is the fluorine as shown in the U.S. Pat. No. 4,427,664 was a merely imaginary one which was thought by referring to its chemical structure on the papers in the specification of said U.S. patent and of which utility for the intended antitumor agent is very much suspicious. Accordingly, we, do not believe that such special compound of the formula (b) where X is the fluorine atom could be prepared by the chemical experts according to the disclosure of the U.S. Pat. No. 4,427,664.

Furthermore, in the U.S. Pat. No. 4,427,664 specification, there is described by the inventors, Horton et al that the compounds of the formula (b) exhibit the antitumor activities against mouse blood cancer cell, Leukemia P 388. More particularly, this U.S. patent specification describes such antitumor activity of 7-O-3,4-di-O-acetyl-2,6-dideoxy-2-ikodo-α-L-mannohexopyranosyl) daunomycinone (nominated as Compound NSC 331,962 by Horton et al) as tested against Leukemia P 388 but does not describe any data of the antitumor activity of 7-O-(3,4-di-O-acetyl-2,6-dideoxy-2-iodo-α-L-talohexopyranosyl)daunomycinone (nominated as Compound NSC 327,472 by Horton et al). While, according to an article of Horton et al reported in the "Carbohydrate Research" Vol. 136, pp. 391-396 (1985), they obtained experimental results to show that said Compound NSC 331,962 exhibited an antitumor activity that the increase (in %) of survival days of the mice treated, as compared to the mice untreated (control) (namely, T/C, %), was 247% at a dosage of 50 mg/kg of the test compound when the mice as inoculated with Leukemia P 338 were treated by administration of the test compound; and that said Compound NSC 331,962 exhibited an antitumor activity that the increase (in %) of survival days of the mice treated, as compared to the mice untreated (T/C, %), was 196% at a dosage of 25 mg/kg of the test compound when the mice as inoculated with Leukemia L-1210 -were treated by administration of the test compound (a single dose per day, intraperitoneally given for 9 days). Also, the above-mentioned Compound NSC 327,472 experimentally showed such antitumor activities that the increase (%) of survival days of the Leukemia P 388-inoculated mice treated was 172% at a dosage of 12.5 mg/kg to 25 mg/kg of Compound NSC 327,472, whereas the increase (%) of survival days of the Leukemia P 388-inoculated mice treated decreased to 162% at a further increased dosage of 150 mg/kg of the tested compound.

Apart from the above-mentioned researches of Horton et al, we have made studies in an attempt to produce new daunomycin derivatives or adriamycin derivatives which have better antitumor activity and lower toxicity than daunomycin and adriamycin. As a result, we already succeeded to synthetize a few examples of such daunomycin derivative and adriamycin derivative in which the sugar moiety of daunomycin or adriamycin has chemically been modified and which are useful as the antitumor agent. Thus, we reported 4'-O-tetrahydropyranyl-daunomycins and -adriamycins (Japanese patent publication No. 47194/81); and 3'-deamino-3'-morpholino-daunomycins and -adriamycins (Japanese patent application first publication "KOKAI" No. 163393/82).

Further, we have made another studies to provide new compounds which are derived by chemical modification with a fluoro group of the 3'-position or 2'-position of kanamycin A and kanamycin B of the aminoglycosidic antibiotics. Thus, we have succeeded to synthetize 3'-deoxy-3'-fluorokanamycin A (Japanese patent application No. 161615/84; U.S. patent application Ser. No. 758,819; European patent application No. 85 4015757.7); 3'-deoxy-3'-fluorokanamycin B (Japanese patent application No. 262700/84); and 2',3'-dideoxy-2'-fluorokanamycin A (Japanese patent application No. 263759/84; U.S. Pat. application Ser. No. 807,485; European patent application No. 85 115901.2).

In this way, we already obtained many findings and experiences in the fluorine chemistry of sugars through our studies where the fluoro group is introduced into kanamycins of the glycosidic antibiotics. Based on these findings and experiences, we have now succeeded to synthetize as a new compound a 4-O-benzyl-protected derivative of methyl 2,6-dideoxy-2-fluoro-α-L-idopyranoside represented by the formula

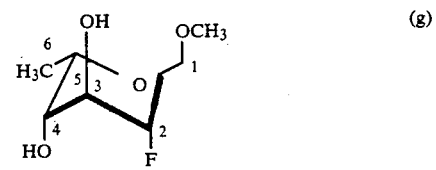

through a multi-stage process with starting from L-fucose of the formula

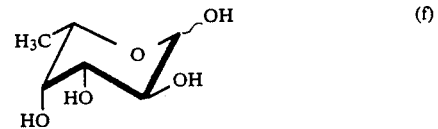

Further, we succeeded to synthetize from the sugar compound of the above formula (g) methyl 2,6-dideoxy-2-fluoro-α-L-talopyranoside of the formula

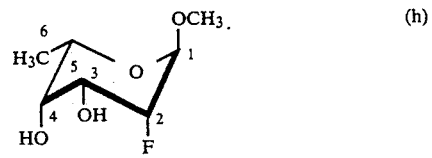

as a new compound, and further synthetize from the compound of the formula (h) 2,6-dideoxy-2-fluoro-α,β-L-talopyranose of the formula

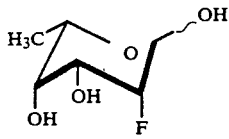

as a new compound and also a 3,4-di-O-protected-2,6-dideoxy-2-fluoro-α-L-talopyranosyl halide of the formula

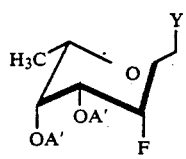

wherein A' is a hydroxyl-protecting group, particularly an acyl group, especially a lower alkanoyl group such as acetyl or an aroyl group such as benzoyl and Y is a chlorine bromine or iodine atom, for example, 3,4-di-O-acetyl-2,6-dideoxy-2-fluoro-α-L-talopyranosyl bromide as a new compound.

Then, we have now succeeded to produce firstly 7-O-(2,6-dideoxy-2-fluoro-α-L-talopyranosyl)-daunomycinone of the formula

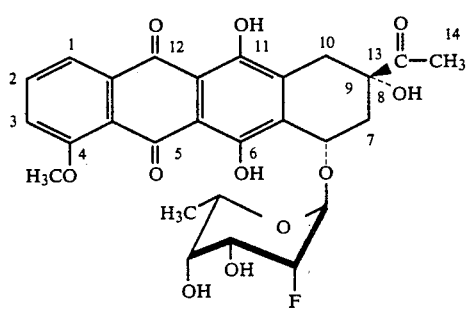

as a new compound by reacting the 3,4-di-O-protected-2,6-dideoxy-2-fluoro-α-L-talpyranosyl halide of the above formula (j) with the 7-hydroxyl group of daunomycinone and then removing the residual hydroxyl-protecting groups (A') from the resulting reaction product.

Furthermore, by converting the 14-methyl group of the compound of the above formula (k) into a hydroxymethyl group (—CH₂OH) by treatment with a mild oxidizing agent, we have now succeeded to produce firstly 7-O-(2,6-dideoxy-2-fluoro-α-L-talopyranosyl)adriamycinone of the formula

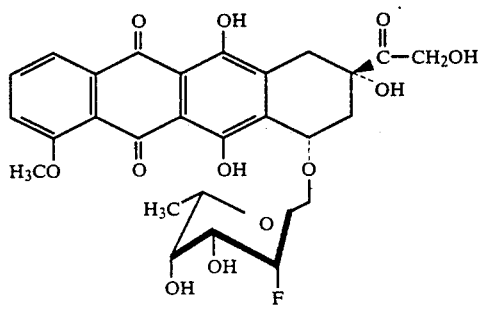

as a new compound. We also have found that the new compound of the formula (k) and the new compound of the formula (l) have excellent antitumor activities and low toxicities and that the glycoside linkage at the 7-hydroxyl group of these new compounds shows a high stability against hydrolysis by acid. Accordingly, the new compound of the formula (k) and the compound of the formula (l) are interesting for use as antitumor agent owing to their low toxicities coupled with their excellent antitumor activities as demonstrated hereinafter. These new compounds of the formulae (k) and (l) have also high antibacterial activities and are useful as antibacterial agent.

Accordingly, there is provided an anthracycline derivative represented by a general formula

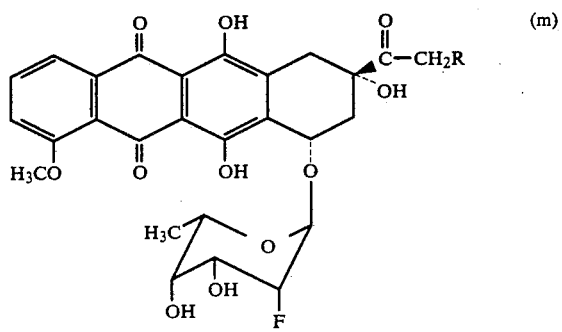

wherein R is a hydrogen atom or a hydroxyl group (Japanese patent application No. 282798/85; U.S. patent application Ser. No. 942,773; European patent application No. 86 117 662.6).

Of the compounds of the general formula (m), 7-O-(2,6-dideoxy-2-fluoro-α-L-talopyranosyl)daunomycinone of the formula (k) is in the form of red colored solids having a specific optical rotation $[\alpha]_D^{25} + 197°$ (c 0.02, chloroform-methanol (1:1)). 7-O-2,6-dideoxy-2-fluoro-α-L-talopyranosyl)adriamycinone of the formula (l) is in the form of red colored solid having a specific optical rotation $[\alpha]_D^{25} + 194°$(c 0.01, chloroform-methanol (1:1)).

We have confirmed by animal tests that the compounds of formula (m) exhibit significantly high antitumor activities on experimental tumors and that the level of their antitumor activities is much higher than those of daunomycin and adriamycin, coupled with an acceptably low level of toxicities. Some typical tests on experimental animal tumors are given below.

TEST 1

Antitumor activity on Leukemia in $CDF_1$ mice caused by Leukemia L-1210 cells

In this test, Compounds of formula (m) were assessed in comparison with daunomycin and adriamycin on their tumor inhibitory activity against leukemia in mice Thus, $CDF_1$ mice were intraperitoneally transplanted with cells of Leukemia L-1210 ($1 \times 10^5$ cells/mouse). From 24 hours after i.p. transplantation of L-1210 cells, each compound to be tested was administered intraperitoneally for 9 consecutive days at once per day. Observation was made for 60 days where survival days of each mouse tested were recorded, and percentage increase in life-span of the treated mice, in comparison with control test wherein mice were treated only with the administration of physiological saline, was calculated as T/C %, where T is the mean survival days of the treated animals and C is the mean survival days of the untreated control animals. The test results are shown in Table 1.

TABLE 1

| | % Increase in life-span (T/C) Dose (mg/kg/day) | | | | | |
|---|---|---|---|---|---|---|
| Compound tested | 5 | 2.5 | 1.25 | 0.6 | 0.3 | 0.15 |
| 7-O-(2,6-Dideoxy-2-fluoro-α-L-talopyranosyl)daunomycinone | 184 | 217 | 171 | 125 | 105 | 105 |
| Daunomycin (comparative) | 138* | 171* | 158 | 145 | 112 | 132 |
| 7-O-(2,6-Dideoxy-2-fluoro-α-L-talopyranosyl)adriamycinone | >740 | >352 | 275 | 185 | 182 | 127 |
| Adriamycin (comparative) | 191* | 228 | 222 | 142 | 136 | 123 |

*shows that a toxicity or its sign of the tested compound in the animals tested such as death due to toxicity or weight loss was observed.

Adriamycin used in Text 1 above for comparison purpose is an anticancer agent clinically used in dosage of 0.4–2 mg/kg depending upon the nature of cancer to be treated. When administered to mice inoculated with L-120 cells in dosage of 2.5 mg–5 mg/kg/day, adriamycin exhibits an antitumor effect of a cetain extent, i.e. percentage increase in life-span of 228–191% with appearance of toxicity (see Table 1). In contrast, 7-O-(2,6-dideoxy-2-fluoro-α-L-talopyranosyl)daunomycinone given in the same dosage as above (i.e. 2.5–5 mg/kg/day) shows a percentage increase in life-span of 217–184% with no sign of toxicity, and 7-O-(2,6-dideoxy-2-fluoro-α-L-talopyranosyl)adriamycinone given in the same dosage as above shows a significantly high percentage increase in life-span of >352%->740% with no sign of toxicity. Such superior effects exhibited by the compounds of formula (m) to that of adriamycin are to be noticeable. Based on this, the new, two anthracycline derivatives of formula (m) are believed to have better antitumor activities than those of adriamycin and are expected to be very useful as antitumor agent for clinical applications, including a variety of tumor diseases in human beings to which adriamycin has been applied. On the other hand, Compound NSC 331,962 synthesized by Horton et al. as referred to above exhibits only a level of antitumor activity of percentage increase in life-span of 196% even when administered in such a high dosage as 25 mg/kg/day to mice inoculated with L-1210 cells. This level of antitumor activity is apparently lower than that of adriamycin.

A further advantage of the anthracycline derivatives of the general formula (m) is in that the susceptibility of the glycoside linkage to be broken by acid hydrolysis is very low. This is, we believe, to be one of reasons why the compounds of formula (m) are of low toxicity. Thus, our experiment has shown that Compound of formula (k), when subjected to acid hydrolysis with 1N HCl in a mixture of acetonitrile-water (4:1) at 60° C. for 8 hours, remains substantially as it is, without being decomposed, whereas daunomycin, when subjected to acid hydrolysis with 0.2N HCl in the same mixture of acetonitrile-water at 60° C., is completely decomposed in only 30 minutes due to breakage of the glycoside linkage, resulting in losing its anticancer activity. Of course, a high chemical stability of a compound in vitro is not always related to its stability against hydrolysis in vivo, but it may be assumed in view of high anticancer effects in vivo of the compounds of formula (m) that the glycoside linkage of those compounds is of high stability in vivo, too. In any case, it is true that such high chemical stability of the glycoside linkage of the compounds of formula (m) is advantageous in that it makes the handling of those compounds easy in chemical applications. Test 2 given below illustrates the high stability of the glycoside linkage of the compounds of formula (m).

TEST 2

(i) Acid hydrolysis of daunomycin

Daunomycin (1 mg) was dissolved in a mixture of (0.1 ml) of 0.2N*HCl-80% $CH_3CN$-$H_2O$ (*the concentration of HCl being 0.2N in the whole mixture) and the solution was heated in oil bath at 61°–62° C. for 30 minutes to cause the hydrolysis. Analysis of the reaction solution by silica gel thin layer chromatography (TLC) showed disappearance of the spot of daunomycin, but appearance of both the spot of daunomycinone and a spot possibly of the sugar moiety which appears at Rf=0 when eluted with benzene-acetone (1:1 by volume) as eluent and which was colored in black by spraying with sulfuric acid followed by heating. The reaction solution was allowed to stand at room temperature to deposit daunomycinone as red crystals.

(ii) Acid hydrolysis of 7-O-(2,6-dideoxy-2-fluoro-α-L-talopyranosyl)-daunomycinone (abbreviated as FTDM)

FTDM (0.7 mg) was suspended in a mixture (0.1 ml) of 0.2N HCl-80% $CH_3CN$-$H_2O$ and suspension was stirred in an oil bath at 61°–62° C. for 30 minutes. Analysis of the reaction mixture by TLC showed the presence of the spot of FTDM only.

A further amount (0.3 ml) of the mixture of 0.2N HCl-80% $CH_3CN$-$H_2O$ was added to the reaction mixture, when the mixture substantially became as solution with a little amount of insolubles. Then, it was heated to 61°–62° C. under stirring to give a homogeneous solution. The solution was then heated at that temperature for further 3 hours and analyzed by TLC with the result that there appeared the spot of FTDM only.

An amount (0.23 ml) of a mixture of 2.4N HCl-80% $CH_3CN$-$H_2O$ was then added to the resulting solution, where the overall concentration of HCl became 1N HCl, and the mixture was further heated in an oil bath at 61°–62° C. for 8 hours and then analyzed by TLC with the result that a spot of a trace amount of daumonycinone appeared, but most of FTDM was remaining at it was.

In our opinion, the high stability against hydrolysis of the glycoside linkage of the anthracycline compounds of formula (m) is attributable to the presence of fluoro group attached on the 2'-position of the sugar moiety of the compounds. It is well-known in the art that amongst elements of halogens, fluorine is a unique element as compared with other halogens and thus cannot be dealt with in chemical behavior on the same level as other halogens. It is also known from the point of view of physical chemistry that the electro-negativity ($\chi$) of fluorine is 4.0 and those of chlorine, bromine and iodine are 3.0, 2.8 and 2.5, respectively, and the bond energy of C-F bond is 116 Kcal/mole and those of C-Cl, C-Br and C-I bondes are 77, 64 and 51 Kcal/mole, respectively. The 2'-fluoro group on the sugar moiety of the compound of the formula (m) strongly attracts electrons into the fluorine atom through the C-F bond due to such a high electro-negativity of fluroine, as a result of which the electron density of the oxygen atoms attached to the 1'-carbon atom of the sugar moiety is lowered and thus these two oxygen atoms show a tendency not to attract any proton H+ from outside, so that the glycoside linkage adjacent to the 1'-carbon atom becomes difficult to be broken by hydrolysis, and in other words, the stability of the glycoside linkage against hydrolysis has been enhanced. Further, the 2'-fluoro group and the oxygen atom of the glycoside linkage attached to the 1'-carbon atom are in antiperiplanar relation, so that the former has a very high power for attracting electrons from the latter. Accordingly, the 2'-fluoro group on the sugar moiety of the anthracycline compounds of formula (m) can have a significant effect for enhancing the stability against acid hydrolysis of the glycoside linkage adjacent to the 1'-carbon atom. Such glycoside linkage-stabilizing effect of the 2'-fluoro group is thus much higher than that of the 2'-iodo group in the above-mentioned Compound NSC 331,962 and Compound NSC 327,472, both synthesized by Horton et al.

Further according to our thought, the reason why the compounds of formula (m) characterized by the 2'-fluoro group on the sugar moiety can exhibit antitumor activities much higher than those exhibited by the abovesaid Compound NSC 331,962 and Compound NSC 327,472 of Horton et al. may be explained as follows:

The fluorine atom attached to the 2'-carbon atom of the compounds of formula (m) has a Van Der Waals' radium (i.e. a value indicating the bulkiness of an atom) of 1.35. This value is next to that of hydrogen atom being 1.20 which is the smallest radius and is far smaller than those of chlorine, bromine and iodine atoms being 1.81, 1.95 and 2.15, respectively. According to the Arcamone's opinion given in his paper "Doxorubicin" (see "Medicinal Chemistry", Ser. 17 (1981) published by Academic Press, New York), it is suggested that the presence of a substituent at the 2'-position on the sugar moiety of daunomycins makes their antitumor activities lower or null. It is quite surprising from Arcamone's suggestion above that the compounds of the general formula (m) exhibit significantly high antitumor activites insite of the presence of the 2'-substituent. One possible explanation for this is such that the bulkiness of the fluorine atom as the 2'-substituent in the compounds of formula (m) is very low, i.e. 1.35 as expressed in term of Van der Waals' radius, which is next to the lowest value 1.20 for hydrogen atom, so that the presence of the 2'-fluoro substituent of such low bulkiness gives little or a little influence only on the space and steric configurations of the molecule of the compounds, that is, no steric hindrance occurs, thus resulting in no deactivation of the desired antitumor activities of the compounds. In view of this, it may also be explained that anthracycline compounds having similar structure to that of the compounds of the general formula (m) but having the 2'-chloro, 2'-bromo or 2'-iodo substituent in place of the 2'-fluoro substituent have appreciably lower antitumor activities than those of the compounds of the general formula (m).

As is clear from the test result given above, the compounds of the general formula (m) exhibit excellent antitumor activities of Leukemia L-1210 cells and experimental animal tumors.

Therefore, the compounds of the general formula (m) can be used as antitumor agents, particularly for treatment of malignant tumors, including solid tumors and ascites tumors.

Now, the production of the compound of the formula (m) is described.

Of the compounds of the formula (m), such compound of the formula (m) where R is then hydrogen atom, specifically the 7-O-(2,6-dideoxy-2-fluoro-α-L-talopyranosyl) daunomycinone of the above formula (k) may be synthetized by reacting a 3,4-di-O-protected-2,6-dideoxy-2-fluoro-α-L-talopyranosyl halide described hereinbefore or a deprotected product thereof represented by the formula (o) shown below, with the 7-hydroxyl group of daunomycinone of formula (n) given below, and then removing the residual hydroxyl-protecting groups from the reaction product obtained, where such residual hydroxyl-protecting groups are remaining in the reaction product.

Thus, the production of an anthracycline derivative represented by the formula

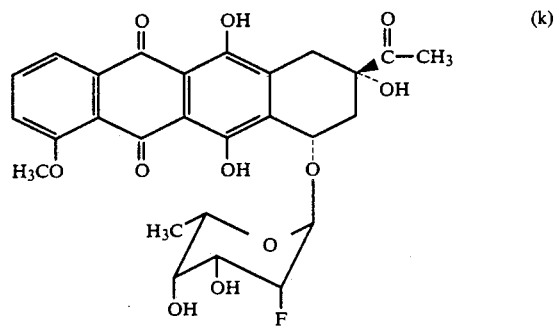

may be conducted by a process which comprises reacting daunomycinone of the formula

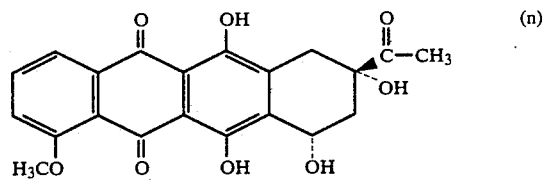

with a 2,6-dideoxy-2-fluoro-α-L-talopyranosyl halide of the formula

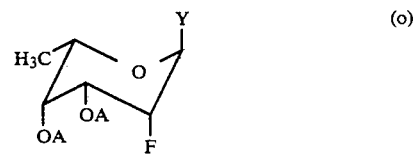

wherein Y is a bromine, iodine or chlorine atom and A is a hydroxyl-protecting group or a hydrogen atom, to produce an anthracycline derivative of the formula

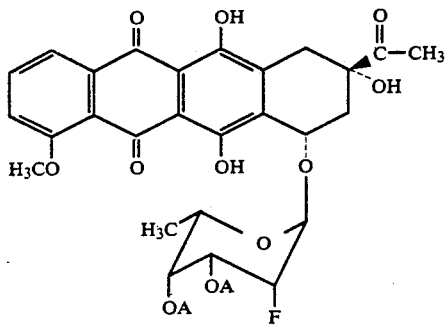

(p)

wherein A is as defined above, and then removing the hydroxyl-protecting groups (A) from the compound of the formula (p) in a known manner, when the compound of the formula (p) is containing the hydroxyl-protecting groups (A) remaining therein.

In the above-mentioned process, the reaction between daunomycinone of formula (n) and a 2,6-dideoxy-2-fluoro-α-L-talopyranosyl halide or its 3,4-di-O-protected derivative of formula (o) may be carried out by a known process for condensing an aglycone with a sugar through a glycoside linkage.

According to this process, in general, the reaction between daunomycinone of formula (n) and a compound of formula (o) may usually be effected in an aprotic organic solvent such as N,N-dimethylformamide (hereinafter referred to as DMF), dimethylsulfoxide, hexamethylphosphoric triamide, diglyme, tetrahydrofuran, dioxane and various halogenated hydrocarbons such as dichloromethane, chloroform, dichloroethane, trichloroethane and tetrachloroethane. Desirably, such aprotic solvent is dried to be free from water before use, although the presence of a little amount of water therein is acceptable.

Usually, the said condensation reaction is desirably carried out in the presence of a dehydrohalogenation agent, for example, tertiary amines such as tertiary alkylamines, e.g. triethylamine, and dimethylaniline., trimethylsilyl triflate, silver oxide, silver trifluoromethanesulfonate, silver carbonate, mercuric oxide, mercuric bromide and mercuric cyanide.

The amount of such dehydrohalogenation agent to be used may generally be at least 1 mole, preferably 2.5–4.0 moles per mole of the halide compound of formula (o).

The amount of the compound of formula (o) to be used is desirably in a slight excess to the stoichiometric amount, for example, 1.5 moles per mole of the compound of formula (n).

The reaction temperature is not so limitative, but may generally be in the range from the freezing point of the solvent used to 80° C. and conveniently at or around the room temperature. Preferably, the reaction between the compound of formula (n) and a compound of formula (o) is carried out in an aprotic organic solvent, typically a halogenated hydrocarbon such as dichloromethane, chloroform, dichloroethane, trichloroethane and tetrachloroethane, under anhydrous conditions, in the presence of a condensation catalyst such as mercuric oxide and mercuric bromide and preferably in the co-presence of a molecular sieve as dehydrating agent. In this preferred embodiment of the process the reaction may be effected by using daunomycin one of formula (n) and a compound of formula (o) in equimolar proportion or in a slight excess proportion of the latter to the former. The reaction temperature may be in the range of −20° C. to 50° C. The reaction product of formula (p) may be recovered from the reaction solution in a usual manner. The reaction product of formula (p) thus recovered may be purified by column chromatography on silica gel using a mixture of benzene and acetone as eluent.

When the compound of formula (p) contains the hydroxyl-protecting groups remaining therein, the protecting groups may be removed by any known deprotecting method. The hydroxyl-protecting groups (A) each are usually an acyl group which may be removed by hydrolysis in the presence of an alkali metal hydroxide such as sodium hydroxide and water.

The resulting compound of formula (k), 7-O-(2,6-dideoxy-2-fluoro-α-L-talopyranosyl)daunomycinone, is in the form of a red solid and may be purified by reprecipitation or recrystallization from a mixture of organic solvents such as chloroform-hexane.

Such a compound of the general formula (m) where R is hydroxyl, namely 7-O-(2,6-dideoxy-2-fluoro-α-L-talopyranosyl)adriamycinone of formula (l) above, may be synthetized by converting the 14-methyl group of either the compound of formula (p) obtained as an intermediate by the process as described hereinbefore or the compound of formula (k) obtained in said process as final product, into a hydroxymethyl (—CH₂OH) group and, if the product so converted contains the hydroxyl-protecting groups remaining therein, by removing the said hydroxy-protecting groups from the product. In this case, the conversion of the 14-methyl group into a hydroxymethyl group is carried out in the following manner. Firstly, the 14-methyl group is brominated with bromine. Organic solvent to be used for said bromination reaction may be halogenated hydrocarbons such as dichloromethane; lower alkanols such as methanol and ethanol; and ethers such as dioxane and tetrahydrofuran. The bromination reaction may be conducted at a temperature in the range of 0°–50° C. It is desirable for said bromination reaction to adopt Arcamone's method in which the reaction is effected in the presence of an alkyl orthoformate (refer to Japanese Patent Publication No. 36919/82). In such a case, the 13-carbonyl group appears to be protected by being converted in the form of dimethylketal. The brominated product (of the ketal type at the 13-carbonyl group) thus obtained (i.e. the 14-bromo-substituted product) is then decomposed with an acid or acetone to restore the original ketone group (i.e. the 13-carbonyl group). When acetone is used for this purpose, the acetone is reacted with the 3- and 4-hydroxyl groups on the talose moiety of the 14-bromo-substituted product to form 3', 4'-O-isopropylidene derivative, which is then treated with an acid to remove the isopropylidene group. Then, the bromo-substituent on the 14-bromo methyl group is converted into a hydroxyl group by the action of sodium formate. If, in such conversion step, the 14-O-formyl group is occasionally formed by side reaction, the 14-O-formyl group is converted into hydroxyl group by treatment with a weak acid or weak alkali (refer to Japanese Patent Publication No. 36919/82).

In cases where the compounds of formula (p) contains hydroxyl-protecting groups (A), the said protecting groups (A) may first be removed if desired, and then the 14-methyl group may be oxidized into the hydroxymethyl group. Alternatively, the 14-methyl group of said compounds of formula (p) may first be oxidized and then the remaining hydroxyl-protecting group (A) may be removed. The removal of the hydroxyl-protecting groups (A) may be effected by hydrolysis in a usual manner.

DETAILED DESCRIPTION OF THE INVENTION 2,6-Dideoxy-2-fluoro-α-L-talopyranosyl halides and 3,4-di-O-protected derivatives thereof according to formula (o) above which are employed in the processes for the production of the new anthracycline compounds of the general formula (m) as described hereinbefore, as well as the precursors thereof, namely methyl 2,6-dideoxy-2-fluoro-α-L-talopyranoside of formula (h) and 2,6-dideoxy-2-fluoro-α-L-talopyranose of formula (i) are each a new compound and are useful as an intermediate product for use in the synthesis of the antitumor compounds of formula (m). Besides, we have now found that the compounds of formula (h) and formula (i) by themselves exhibit a higher antibacterial activity against some species of bacteria than that of phenol which is known as disinfecting agent so that they are useful as antibacterial agent or disinfecting agent.

According to a first aspect of this invention, therefore, there is provided 2,6-dideoxy-2-fluoro-L-talopyranose or derivatives thereof represented by the general formula (I)

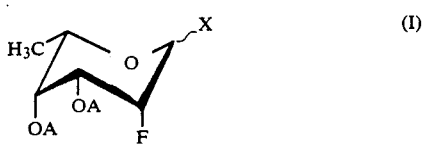

wherein A is a hydrogen atom or a hydroxyl-protecting group, preferably an acyl group, for example, a lower alkanoyl group such as acetyl or an aroyl group such as benzoyl, and X is a hydroxyl group or a methoxy group, or chlorine, bromine or iodine atom, as a class of new compounds which include the compound of formula (h), the compound of formula (i) and the compound of formula (o) above.

Of the new compounds of the formula (I) according to this invention, methyl 2,6-dideoxy-2-fluoro-α-L-talopyranoside of formula (h) is a crystalline substance having a melting point of 112°-114° C. and a specific rotation $[\alpha]_D^{23}$ —124° (c 1, methanol).

2,6-Dideoxy-2-fluoro-α,β-L-talopyranose of formula (i) which is covered by the compounds of formula (I) according to this invention is a colorless solid substance having a specific rotation $[\alpha]^{25}{}_D -21°$ (c 1, dioxane-water, 4:1).

3,4-Di-O-acetyl-2,6-dideoxy-2-fluoro-α-L-talopyranosyl bromide of the formula

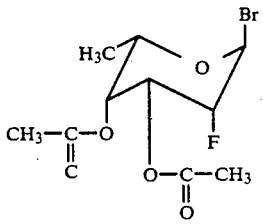

which is also covered by the compound of formula (I) according to this invention is a syrupy substance having a specific rotation $[\alpha]^{25}{}_D - 154°$ (c 1, chloroform).

Minimum inhibitory concentrations (MIC., mcg/ml) of the new compounds of formulae (h) and (i) against the growth of some species of bacteria have been determined according to a standard serial dilution method. The MIC. data of these new compounds so determined are shown in Table 2 below.

TABLE 2

| Test organisms | MIC. (mcg/ml) | |
| --- | --- | --- |
| | Compound of formula (h) | Compound of formula (i) |
| *Micrococcus luteus* ATCC 9341 (MS-1) | 100 | Not tested |
| *Salmonella paratyphi* 1015 (MS-1) | 100 | 100 |
| *Corynebacterium bovis* 1810 | Not tested | 100 |

For the production of such a compound of the formula (I) where A is hydrogen atom and X is methoxy group, namely the compound of the aforesaid formula (h) [hereinafter referred to as compound of formula (Ia)], there is provided according to the second aspect of this invention a process for the production of methyl 2,6-dideoxy-2-fluoro-α-L-talopyranoside of the formula

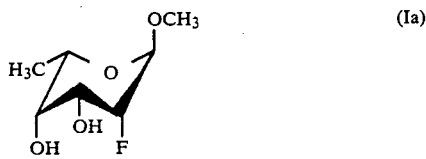

which comprises the steps of:
(a) reacting potassium hydrogen fluoride or sodium hydrogen fluoride with a methyl 2,3-anhydro-4-O-protected-6-deoxy-α-L-gulopyranoside of the formula

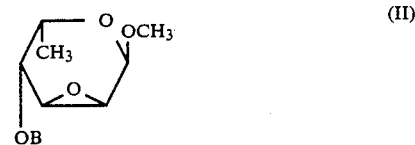

wherein B is a hydroxyl-protecting group, preferably an aralkyl group, to produce a methyl 4-O-protected-2,6-dideoxy-2-fluoro-α-L-idopyranoside of the formula

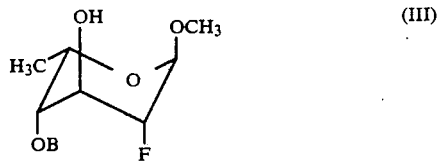

wherein B is as defined above,
(b) reacting the compound of formula (III) above with an oxidizing agent to produce a methyl 4-O-protected-2,6-dideoxy-2-fluoro-α-L-lyxo-hexopyranoside-3-ulose of the formula

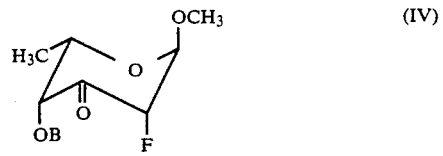

wherein B is as defined above, (c) reacting the compound of formula (IV) with a reducing agent to produce a methyl 4-O-protected-2,6-dideoxy-2-fluoro-L-talopyranoside of the formula

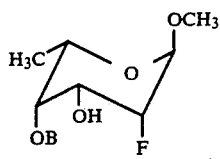

wherein B is as defined above, and (d) removing the hydroxyl-protecting group (B) from the compound of formula (V) to produce the compound of formula (Ia) above.

The methyl 2,3-anhydro-4-O-protected-6-deoxy-α-L-gulopyranoside of formula (II) which is employed as a starting compound in the above-mentioned process according to the second aspect of this invention may be methyl 2,3-anhydro-4-O-benzyl-6-deoxy-α-L-gulopyranoside which is prepared by the procedures of Example 1, (1) to (6) described hereinafter.

The benzyl group which is existing as the hydroxyl-protecting group (B) in the above-mentioned methyl 2,3-anhydro-4-O-benzyl-6-deoxy-α-L-gulopyranoside can be replaced by a hydroxyl-protecting group of another nature, for example, one of an acyl type, according to such a method wherein said benzyl group is removed by catalytic hydrogenolysis according to a known deprotecting technique and subsequently the liberated 4-hydroxyl group is again protected by a second hydroxyl-protecting group of another nature as introduced by a known technique for protection of hydroxyl group.

In the process according to the second aspect of this invention, the reaction of potassium hydrogen fluoride or sodium hydrogen fluoride with the compound of formula (II) may be conducted in an appropriate organic solvent, for example, glycols such as lower alkylene glycols, especially ethylene glycol, propylene glycol and 2,3-dihydroxybutane at a temperature of 100° to 250° C. The amount of potassium or sodium hydrogen fluoride to be used may be in a proportion of 5 to 30 mol per mol of the compound of formula (II). After completion of the reaction, the reaction solution containing the desired reaction product of formula (III) may be diluted with chloroform, washed with aqueous sodium hydrogen carbonate and then with water and subsequently distilled to remove the organic solvents therefrom. The reaction solution is thus concentrated to dryness and the residue obtained is purified by silica gel chromatography to give a purified product of the compound of formula (III).

Next, the reaction of oxidizing the 3-hydroxyl group of the compound of formula (III) so obtained is performed. The oxidizing agent for this reaction may suitably be dimethylsulfoxide or pyridinium chlorochromate. This oxidation reaction may be carried out in dimethylsulfoxide or a mixture of benzene and an excess of dimethylsulfoxide at room temperature. Preferably, the oxidation reaction may be conducted in the presence of pyridine and pyridinium trifluoroacetate which serve as the catalyst, and in the presence of dicyclohexlcarbodiimide which serves as a reaction promotor. After completion of the reaction, the reaction solution may be mixed with a methanolic solution of oxalic acid to decompose the excess of the dicyclohexylcarbodiimide. The resulting admixture is then diluted with benzene and filtered to remove the insoluble matters as formed, and the filtrate is distilled to remove the solvents therefrom. The residue obtained is purified by silica gel chromatography to afford a purified product of the compound of formula (IV).

Subsequently, the reaction of converting the oxo group attached to the carbon atom at the 3-position of the compound of formula (IV) into the hydroxyl group is conducted by treatment with a reducing agent. Through this reduction reaction, there is formed the compound of formula (V) of which the 3-hydroxyl group is oriented opposite to the 3-hydroxyl group present in the compound of formula (III).

The reducing agent suitable for the above-mentioned reduction reaction includes lithium aluminum hydride and other metal hydrides such as lithium borohydride and sodium cyanoborohydride. The reduction reaction may be carrried out at a temperature of −30° C. to +30° C. in a reaction medium comprising tetrahydrofuran, ethyl ether or diglyme. After completion of the reduction reaction, the reaction solution is mixed with aqueous ammonium chloride to decompose the metal hydride which was used as the reducing agent but is remaining unreacted. The reaction solution so treated is then extracted with chloroform to afford a solution of the compound of formula (V) in chloroform as the extract. This extract solution is washed with water and distilled to remove the chloroform. The residue obtained may be purified by silica gel chromatography to give a purified product of the compound of formula (V).

Where the compound of formula (V) obtained is containing the remaining hydroxyl-protecting group (B), this compound is deprotected in a known manner by a proper deprotecting technique to produce the desired methyl 2,6-dideoxy-2-fluoro-α-L-talopyranoside of formula (Ia).

The methyl 4-O-protected-2,6-dideoxy-2-fluoro-α-L-lyxo-hexopyranosid-3-ulose of formula (IV) which is produced as an intermediate product in the above process of the second aspect of this invention is also a new compound and is possible to be prepared by a such a route different from the above-mentioned particular process where the starting compound of formula (II) is converted into the compound of formula (III) and the latter is then converted into the compound of formula (IV) as shown above.

Therefore, as an independent process of producing the compound of formula (Ia) which is not limited to the aforesaid particular procedure of preparing the starting compound of formula (IV), there is provided according to the third aspect of this invention a process for the production of methyl 2,6-dideoxy-2-fluoro-α-L-talopyranoside of the formula

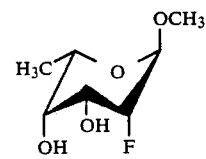

which comprises the steps of:

(i) reacting a reducing agent with a methyl 4-O-protected-2,6-dideoxy-2-fluoro-α-L-lyxo-hexopyranosid-3-ulose of the formula

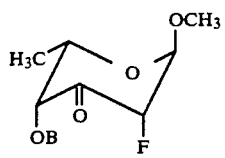

(IV)

wherein B is a hydroxyl-protecting group to produce a methyl 4-O-protected-2,6-dideoxy-2-fluoro-α-L-talopyranoside of the formula

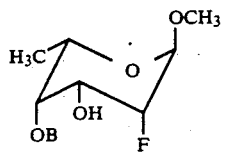

(V)

wherein B is as defined above, and (ii) removing the hydroxyl-protecting group (B) from the compound of formula (V) to produce the compound of formula (Ia) above.

In the process according to the third aspect of this invention, the step (i) of reacting the compound of formula (IV) with the reducing agent and the step (ii) of removing the residual hydroxyl-protective group (B) from the resulting compound of formula (V) may be performed in the same manner as the corresponding step (c) and (d) of the process of the second aspect of this invention as described hereinbefore.

Furthermore, amongst the compounds of formula (I) according to the first aspect of this invention, such compound of formula (I) where A is a hydrogen atom and X is a hydroxyl group, namely 2,6-dideoxy-2-fluoro-α-L-talopyranose of formula (i) shown hereinbefore may be produced by hydrolyzing methyl 2,6-dideoxy-2-fluoro-α-L-talopyranoside of formula (h) in trifluoroacetic acid containing hydrochloric acid so that the 1-methoxy group of the compound of formula (h) is converted into the hydroxyl group. The hydrolysis reaction for this purpose may be carried out in the reaction medium comprising trifluoroacetic acid under acidic condition in the presence of hydrochloric acid and water at a temperature of 40° C. to 80° C. Some parts of the hydrolysis product as formed in this hydrolysis reaction contain the 1-hydroxyl group of which the steric orientation is reversed opposite to the original orientation of the 1-methoxy group present in the compound of formula (h). Thus, the compound of formula (i) as formed is actually composed of a mixture of 2,6-dideoxy-2-fluoro-α-L-talopyranose and 2,6-dideoxy2-fluoro-β-L-talopyranose. The α-isomer and β-isomer of said mixture cannot be isolated from each other by chromatographic method as far as we have tried presently.

Amongst the compounds of formula (I) according to the first aspect of this invention, such compounds of formula (I) where A is a hydrogen atom and X is a halogen atom, that is, the 2,6-dideoxy-2-fluoro-α-L-talopyranosyl halides according to the formula (o) where A is the hydrogen atom and Y is a halogen are each a new compound and may be produced using the methyl 2,6-dideoxy-2-fluoro-α-L-talopyranoside of formula (h) as a starting compound and treating the latter compound in the following process. Thus, for instance, methyl 2,6-dideoxy-2-fluoro-α-L-talopyranoside of formula (h) as prepared by the procedure of Example 2, (4) given hereinafter is treated by reacting with acetic anhydride in the presence of sulfuric acid to form 1,3,4-tri-O-acetyl-2,6-dideoxy-2-fluoro-α-L-talopyranose of the formula

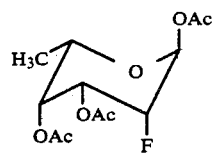

(r)

wherein Ac is acetyl. The compound of formula (r) is then reacted with a titanium tetrahalide such as titanium tetrabromide, titanium tetrachloride or titanium tetraiodide in an inert organic solvent such as dichloromethane, ethyl acetate or preferably a mixture of them under anhydrous conditions at room temperature or under heating, or alternatively is reacted with hydrogen bromide or hydrogen chloride in the form of a solution in acetic acid, whereby to form a 3,4-di-O-acetyl-2,6-dideoxy-2-fluoro-α-L-talopyranosyl halide of the formula

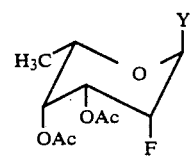

(s)

wherein Ac is acetyl and Y is chlorine, bromine or iodine atom. Finally, the acetyl groups of the resulting compound of formula (s) is removed by hydrolysis in an inert solvent to give a desired, unprotected compound according to the formula (o) shown hereinbefore. The removal of acetyl groups from the compound of formula (s) may, for example, be effected by reacting said compound with an aqueous hydrobromic acid solution. In cases where the compounds of formula (o) are 3,4-di-O-protected derivatives of 2,6-dideoxy-2 fluoro-α-L-talopyranosyl halides, such derivatives may typically be the compound of formula (s) as such, that is, the compound of formula (o) where each A is acetyl as the hydroxyl-protecting group (A).

Compounds of formula (o) where each A is various, acyl groups other than acetyl as hydroxyl-protecting group can be prepared by the process explained above except that the first step for preparing the compound of formula (r) from the compound of formula (h) is modifide by using other lower alkanoic acid anhydrides or chlorides or aromatic carboxylic acid anhydrides or chlorides such as benzoic acid anhydride or chloride, in place of the acetic anhydride to be reacted with the compound of formula (h) so that the methoxy group at the 1-position and the hydroxyl groups at the 3- and 4-positions of the compound of formula (h) are transformed to be protected by the corresponding acyl group. In this way, a 1,3,4-tri-O-acyl-2,6-dideoxy-2-fluoro-α-L-talopyranose may be prepared and this compound may then be reacted with a titanium tetrahalide to prepare a compound of formula (o) where A is generally an acyl group as the hydroxyl-protecting group and Y is a halogen atom.

A process of preparing an illustrative compound of a methyl 2,3-anhydro-4-O-protected-6-deoxy-2-fluoro-α-L-gulopyranoside of formula (II) shown hereinbefore which is also a new compound is illustratively given in Example 1, (1) to (6) as described hereinafter.

The following Examples concretely illustrate the production of the new compounds of the general formula (I) according to this invention, as well as the preparation of a series of intermediates to be used for the preparation of the compounds of formula (I) starting from L-fucose. Thus, Examples 1 and 2 illustrates the preparation of methyl 2,6-dideoxy-2-fluoro-α-L-talopyranoside of formula (h) starting from L-fucose; Example 3 shows the preparation of 2,6-dideoxy-2-fluoro-L-talopyranose of formula (i); Example 4 shows the preparation of 3,4-di-O-acetyl-2,6-dideoxy-2-fluoro-α-L-talopyranosyl bromide of formula (q); and Examples 5–shows the preparation of the compounds of formula (m).

EXAMPLE 1

Preparation of methyl 2,6-dideoxy-2-fluoro-α-L-talopyranoside (1) Methyl 6-deoxy-3,4-O-isopropylidene-α-L-galactopyranoside

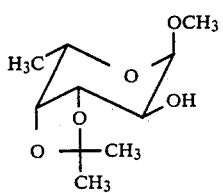

A suspension of L-fucose (2.90 g) in methanol (40 ml) containing 1% hydrogen chloride was heated for 8 hours under reflux. The resulting homogeneous solution was cooled to room temperature, neutralized with the addition of basic lead carbonate and then filtered. The filtrate was concentrated to give a colorless solid (3.04 g) comprising mixture of methyl fucosides. The solid was dissolved in dry dimethylformamide (40 ml), to which were added 2,2-dimethoxypropane (7.81 g) and anhydrous p-toluenesulfonic acid (870 mg),and the reaction was conducted at room temperature for 2 hours. The reaction solution was neutralized with sodium hydrogen carbonate and then filtered to remove the insoluble matters. The filtrate was concentrated in vacuo and the residue obtained was dissolved in chloroform (100 ml). The resulting solution was washed with a saturated aqueous sodium hydrogen carbonate solution and then with an aqueous 10% sodium chloride solution and then concentrated. The residue was treated by silica gel column chromatography on a column of silica gel (400 ml) using a mixture of hexane and acetone (2:1 by volume) as eluent (750–1200 ml),to isolate and purify the titled compound as a syrup. Yield: 2.28 g (59%). $[\alpha]_D^{26} -154°$ (c 1, chloroform) $^1$H-NMR spectrum (deuterochloroform): δ4.72 (1H, d, H-1) $J_{1,2}$ 2 3.5 Hz (2) Methyl 2-O-acetyl-6-deoxy-3,4-O-isopropylidene-α-L-galactopyranoside

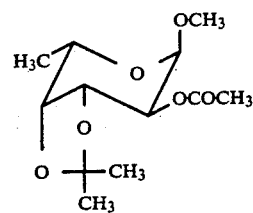

Methyl 6-deoxy-3,4-O-isopropylidene-α-L-galactopyranoside (12.56 g) was dissolved in dry pyridine (35 ml) and acetic anhydride (17 ml) was added to the solution. The reaction was conducted at room temperature for 8 hours, after which water (20 ml) was added to the resulting reaction solution, and the mixture obtained was concentrated in vacuo. The residue was dissolved in chloroform (500 ml) and the solution was washed, successively, with an aqueous 10% potasssium hydrogen sulphate solution, a saturated aqueous sodium hydrogen carbonate solution and water and then concentrated to yield the titled compound (13.81 g; 92%) as colorless crystals. Recrystallization from a mixture of ethyl ether and hexane afforded needle crystals.
mp. 101°–102° C.
$[\alpha]_D^{26} -176°$ (c 1, chloroform)
$^1$H-NMR spectrum (deuterochloroform) δ4.92 (1H, dd, H-2) 4.79 (1H, d, H-1)
Elemental analysis ($C_{12}H_{20}O_6$) Calculated: C 55.37; H 7.74%: Found: C 55.27; H 7.80%

(3) Methy 1 2-O-acetyl-6-deoxy-α-L-galactopyranoside

Methyl 2-O-acetyl-6-deoxy-3,4-O-isopropylidene-α-L-galactopyranoside (13.81 g) obtained as above was dissolved in an aqueous 80% acetic acid solution (140 ml) and the reaction was conducted at 80° C. for 1 hour. The reaction solution was concentrated in vacuo and the resultant residue was treated by silica gel column chromatography on a silica gel column (600 ml) using a mixture of hexane and acetone (1:2 by volume) as eluent(1100–1950 ml), to isolate and purify the titled compound as colorless crystals (11.17 g; 96%). Recrystallization was made from an ethyl ether-hexane mixture.
mp. 77°–78° C.
$[\alpha]_D^{26} -182°$ (c 2, chloroform)

(4) Methyl 2-O-acetyl-6-deoxy-3-O-tosyl-α-L-galactopyranoside

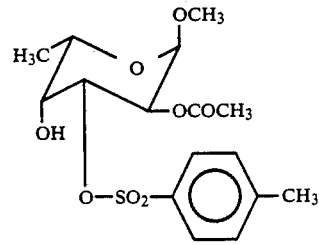

Methyl 2-O-acetyl-6-deoxy-α-L-galactopyranoside (11 g) was dissolved in dry pyridine (200 ml), and to the resulting solution, after cooling to −20° C, was added p-toluenesulfonyl chloride (13.33 g). The reaction was conducted at −20° C. for 26 hours and then at room temperature for 19 hours. The reaction solution, after water ( 5 ml) was added thereto, was concentrated in vacuo. The residue was treated by column chromatography on silica gel column (700 ml) using a mixture of hexane and acetone (1:1 by volume as eluent (1550–2600 ml), to isolate and purify the titled compound as colorless crystals (16.25 g; 87%). Recrystallization was effected from an ethyl ether-hexane mixture.

mp. 118°–120° C.

$[\alpha]_D^{26}$ −136° (c 1, chloroform)

$^1$H-NMR spectrum (deuterochloroform): δ5.16 (1H, dd, H-2) 4.94 (1H, dd, H-3) 4.87 (1H, d, H-1) 2.45 (3H, s, CH$_3$ in tosyl) 1.79 (3H, s, Acetyl)

Elemental analysis (C$_{16}$H$_{22}$O$_8$S$_1$) Calculated: C 51.33; H 5.92; S 8.56%. Found: C 51.41; H 6.06; S 8.65%

(5) Methyl 2-O-acetyl-4-O-benzyl-6-deoxy-3-O-tosyl-α-L-galactopyranoside

Methyl 2-O-acetyl-6-deoxy-3-O-tosyl-α-L-galactopyranoside (160 mg) was dissolved in a mixture (3.2 ml) of cyclohexane and dichloromethane (2:1 by volume), to which were then added benzyl 2,2,2-trichloroacetimidate

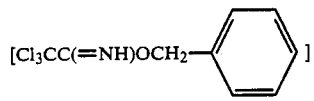

(214 mg) and trifluromethanesulfonic acid (0.015 ml), and the whole mixture was kept at room temperature for 2 hours to effect the reaction. The reaction solution was diluted with chloroform, then washed with a saturated aqueous sodium hydrogen carbonate solution and then with water and finally concentrated. The residue was treated by silica gel column (30 ml) chromatography using a mixture of toluene and ethyl acetate (6:1 by volume, 55–80 ml), to isolate and purify the titled compound as a syrup (164 mg; 83%).

$[\alpha]^{26}_D$ −101° (c 1.5, chloroform)

(6) Methyl 2,3-anhydro-4-O-benzyl-6-deoxy-α-L-gulopyranoside

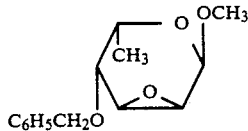

Methyl 2-O-acetyl-4-O-benzyl-6-deoxy-3-O-tosyl-α-L-galactopyranoside (19.72 g) obtained as above was dissolved in dry methanol (400 ml), to which a 28% methanolic solution of sodium methoxide (123 ml) was added, and the resulting mixture was kept at room temperature for 4.5 hours to effect the reaction. The reaction solution, after carbon dioxide was introduced thereinto, was concentrated, and the residue was dissolved in chloroform (300 ml). The solution in chloroform was washed with water and then concentrated. The residue was treated by silica gel column (800 ml) chromatography using a mixture of hexane and acetone (3:1 by volume) as eluent (1350–2550 ml), to isolate and purify the titled compound as a colorless syrup (6.62 g; 62%).

$[\alpha]_D^{26}$ −25° (c 3, chloroform)

EXAMPLE 2

(1) Methyl 4-O-benzyl-2,6-dideoxy-2-fluoro-α-L-idopyranoside

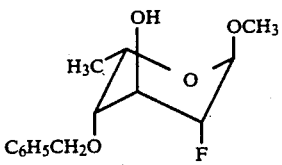

Methyl 2,3-anhydro-4-O-benzyl-6-deoxy-α-L-gulopyranoside (140 mg) as prepared in Example 1(6) was dissolved in dry ethylene glycol (2.8 ml), to which potassium hydrogen fluoride (KHF$_2$) (880 mg) was then added, and the resultant mixture was stirred at 180° C. for 3 hours. The reaction solution obtained was diluted with chloroform, washed with a saturated aqueous sodium hydrogen carbonate and then with water and concentrated. The residue was treated by silica gel column (30 ml) chromatography using a mixture of hexane and acetone (3:1 by volume) as eluent(75–105 ml) to isolate and purify the titled compound as a syrup (67 mg; 44%).

$[\alpha]_D^{26}$ −62° (c 2, chloroform)

$^1$H-NMR spectrum (deuterochloroform): δ4.79 (1H, dd, H-1) 4.32 (1H, dddd, H-2) $^{19}$F-NMR spectrum (deuterochloroform., CFCl$_3$ as internal standard): Φ −196.0 (ddd) J$_{F,H}$-248, J$_{F,H}$-311, J$_{F,H}$-19 Hz Elemental analysis (C$_{14}$H$_{19}$O$_4$F$_1$) Calculated: C 62.21; H 7.08; F 7.03%: Found: C 61.98; H 7.17., F 7.01%

Methyl 4-O-benzyl-2,6-dideoxy-2-fluoro-α-L-lyxo-hexopyranosid-3-ulose

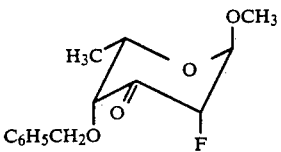

Methyl 4-O-benzyl-2,6-dideoxy-2-fluoro-α-L-idopyranoside (139 mg) obtained as above was dissolved in a mixture of dry benzene (1 ml) and dry dimethylsulfoxide (0.14 ml) which acts as both a solvent and an oxidizing agent. To the resulting solution were added dicyclohexylcarbodiimide (155 mg), pyridine (0.01 ml) and pyridinium trifluoroacetate (23 mg), and the resulting mixture was stirred at room temperature for 3 hours to effect the reaction. The reaction solution was admixed with a methanolic solution of oxalic acid (142 mg) to decompose the excess of the dicyclohexylcarbodiimide. Then, the reaction solution so treated was diluted with benzene (30 ml) and filtered to remove the insolubles. The filtrate was washed with a saturated aqueous sodium hydrogen carbonate solution and then with water, and concentrated. The residue was treated by silica gel column (25 ml) chromatography using a mixture of hexane and acetone (3:1 by volume) as eluent (40–70 ml), to isolate and purify the titled compound as needle crystals (110 mg; 79%).

mp. 63°–64° C.

$[\alpha]_D^{26}$ −7° (c 1, chloroform)

(3) Methyl 4-O-benzyl-2,6-dideoxy-2-fluoro-α-L-talopyranoside

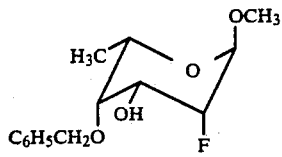

Methyl 4-O-benzyl-2,6-dideoxy-2-fluoro-α-L-lyxo-hexopyranosid-3-ulose (698 mg) was dissolved in dry tetrahydrofuran (14 ml), and to the resulting solution, after cooling to −30° C., was added a suspension of lithium aluminium hydride (198 mg) in dry tetrahydrofuran (2 ml). The mixture was stirred at −30° C. for 45 minutes, then at −10° C. for 2 hours and finally at 0° C. for 30 minutes. A saturated aqueous ammonium chloride solution was then added to the resultant reaction solution as cooled at 0°C., to which chloroform (50 ml) was further added. The resulting mixture was filtered. The chloroform solution thus separated was washed with water and concentrated. The residue was treated by silica gel column (100 ml) chromatography using a mixture of hexane and acetone (3:1 by volume) as eluent, to isolate and purify the titled compound as a thick syrup (576 mg; 82%).

$[\alpha]_D^{26} -98°$ (c 3.5, chloroform) $^{19}$F-NMR spectrum (deuterochloroform; CFCl$_3$ internal standard): Φ−206.0 (ddd) $J_{F,H-2}$ 49.5, $J_{F,H-3}$ 31.5, $J_{F,H-1}$ 9 Hz

Methyl 2,6-dideoxy-2-fluoro-α-L-talopyranoside

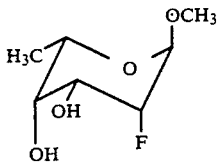

Methyl 4-O-benzyl-2,6-dideoxy-2-fluoro-α-L-talopyranoside (345 mg) obtained as above was dissolved in a mixture (8 ml) of dioxane, acetic acid and water (10:1:1 by volume), and the resulting solution was subjected to catalytic reduction with hydrogen at atmospheric pressure in the presence of palladium black catalyst to remove the benzyl group for the deprotection. The reaction mixture obtained was filtered and the filtrate was concentrated invacuo to yield a colorless solid (230 mg). Recrystallization of this solid from a mixture of chloroform and hexane gave the titled compound as colorless crystals (186 mg; 81%).

mp. 112°–114° C.

$[\alpha]_D^{23} -124°$ (c 1, methanol) $^1$H-NMR spectrum (deuterochloroform): δ4.87 (1H, dd, H-1) δ4.58 (1H, ddt, H-2) $^{19}$F-NMR spectrum (deuterochloroform; internal standard: CFCl$_3$) Φ−203.1 (dddd) $J_{F,H-2}$ 49, $J_{F,H-3}$ 32, $J_{F,H-1}$ 9, $J_{F,OH}$ 7.5 Hz.

EXAMPLE 3

Preparation of 2,6-dideoxy-2-fluoro-L-talopyranose

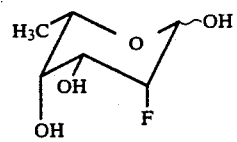

Methyl 2,6-dideoxy-2-fluoro-α-L-talopyranoside (21 mg) as prepared in Example 2 (4) given hereinbefore was dissolved in 1 ml of a mixture of 3N HCl-75% trifluoroacetic acid-water (the concentration of HCl in the whole mixture was 3N), and the resulting solution was heated at 60° C. for 1.5 hours to effect the hydrolysis. The reaction solution was then concentrated under reduced pressure to a smaller volume and the concentrated solution was admixed with a volume of water and azeotropically distilled. The residual solution was then concentrated to dryness to give 18 mg (93%) of the titled compound as a colorless solid. Specific rotation $[\alpha]_D^{25} -21°$ (c 1, dioxane-water, 4:1).

Judging from the NMR spectrum (in deuterodioxane-deutero-water, 4:1) of the title compound so obtained, the resulting hydrolysis product was composed of a mixture of 2,6-dideoxy-2-fluoro-α-L-talopyranose and 2,6-dideoxy-2-fluoro-β-L-talopyranose.

$^1$H-NMR spectrum (in deutero-dioxane-deutero-water, 4:1): The α-isomer: δ5.21 (dd, H-1) δ4.44 (broad d, H-2) The β-isomer: δ4.60 (d, H-1) δ4.52 (broad d, H-2)

$^{19}$F-NMR spectrum (in deutero-dioxane-deutero-water, 4:1; CFCl$_3$ as internal standard): The α-isomer: Φ−201.1 (ddd) $J_{F,H-2}$ 50, $J_{F,H-3}$ 34, $J_{F,H-1}$ 9.5 Hz The β-isomer: Φ−221.4 (ddd) $J_{F,H-2}$ 51.5, $J_{F,H-3}$ 33, $J_{F,H-1}$ 21 Hz It was observed that the ratio of the α-isomer to the β-isomer present in the resulting mixed hydrolysis product of 2,6-dideoxy-2-fluoro-L-talopyranose varied with lapse of time. This hydrolysis product obtained was subjected to silica gel thin layer chromatography, when the α-isomer and the β-isomer could not be separated from each other.

EXAMPLE 4

Preparation of 3,4-di-O-acetyl-2,6-dideoxy-2-fluoro-α-L-talopyranosyl bromide

(1) 1,3,4-Tri-O-acetyl-2,6-dideoxy-2-fluoro-α-L-talopyranose

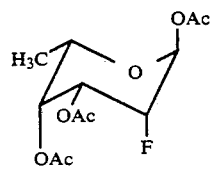

Ac = acetyl

Methyl 2,6-dideoxy-2-fluoro-α-L-talopyranoside (230 mg) which was prepared as in Example 2 (4) was dissolved in dry nitromethane (7.6 ml), to which were added acetic anhydride (1.3 ml) and sulfuric acid (0.036 ml). The resulting mixture was kept at room temperature for 4 hours to effect the acetylation. The reaction solution as neutralized with a saturated aqueous sodium hydrogen carbonate solution and then diluted with chloroform (50 ml). The diluted solution was washed with water and concentrated. The residue was treated by silica gel column (60 ml) chromatography using a mixture of hexane and acetone (3:1 by volume) as eluent (110–175 ml), to isolated and purify the titled compound as colorless crystals (313 mg; 84%). The product was recrystallized from a mixture of ether and hexane.

mp. 102°–103° C.

$[\alpha]_D^{26} -111°$ (c 1, chloroform) $^1$H-NMR spectrum (dueterochloroform): $\delta 6.33$ (1H, dd, H-1) 4.55 (1H, dddd, H-2)

Elemental analysis ($C_{12}H_{17}O_7F$) Calculated: C 49.32; H 5.86; F 6.50%: Found: C 49.19; H 6.00; F 6.39%

(2)
3,4-di-O-acetyl-2,6-dideoxy-2-fluoro-α-L-talopyranosyl bromide

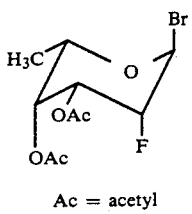

Ac = acetyl 1,3,4-Tri-O-acetyl-2,6-dideoxy-2-fluoro-α-L-talopyranose (327 mg) obtained as above was dissolved in a mixture (7 ml) of dry dichloromethane and dry ethyl acetate (10:1 by volume), to which titanium tetrabromide (534 mg) was added, and the mixture was allowed to stand at room temperature for 22 hours for the reaction. To the reaction solution, there were added, succesively, dry acetonitrile (10 ml), dry sodium acetate (1.67 g) and dry toluene (20 ml). The precipitate thus deposited was removed by filtration and the filtrate was concentrated in vacuo. Dry toluene (20 ml) was added to the residue, and the mixture was filtered to remove the insolubles. The filtrate was concentrated in vacuo to afford the titled compound as a syrup (330 mg; 94%):

$[\alpha]_D^{25} -154°$ (c 1, chloroform) $^1$H-NMR spectrum (deuterochloroform): $\delta 6.55$ (1H, broad d, H-1) 4.81 (1H, ddt, H-2)

EXAMPLE 5

Production of
7-O-(2,6-dideoxy-2-fluoro-α-L-talopyranosyl)-daunomycinone (1)
7-O-(3,4-di-O-acetyl-2,6-dideoxy-2-fluoro-α-L-talopyranosyl) daunomycinone To a suspension of daunomycinone (290 mg), mercuric oxide (yellow color) (943 mg), mercuric bromide (273 mg) and "Molecular Sieves" 3A in powder form (4.5 g) in dry dichloromethane (36 ml), there was added a solution of 3,4-di-O-acetyl-2,6-dideoxy-2-fluoro-α-L-talopyranosyl bromide (330 mg) as prepared in Example 4(2), in dry dichloromethane (9 ml). The resulting mixture was stirred in a dark place at room temperature for 20 hours and filtered. The filtrate was diluted with chloroform and the diluted solution was washed with an aqueous 30% potassium iodide solution, a saturated aqueous sodium hydrogen carbonate solution and water, successively, and concentrated. The residue was treated by silica gel column (60 ml) chromatography using a mixture of benzene and acetone (4:1 by volume) as developing solvent (125–210 ml), to isolate and purify the titled compound as a red solid (378 mg; 82%). This product was reprecipitated from a mixture of chloroform and hexane.

mp. 144°–146° C. $[\alpha]_D^{26} +211°$ (c 0.036, chloroform)

$^1$H-NMR spectrum (deuterochloroform): $\delta 5.64$ (1H, dd, H-1') 4.08 (3H, s, OCH$_3$) 2.41 (3H, s, Acetyl) 2.18, 2.03 (each 3H, s, OAc)

$^{19}$F-NMR spectrum (deuterochloroform; internal standard: CFCl$_3$): $\Phi -201.0$ (ddd) $J_{F,H-2'}$49.5, $J_{F,H-3'}$32.5, $J_{F,H-1'}$9.5 Hz Elemental analysis ($C_{31}H_{31}O_{13}F \cdot H_2O$) Calculated: C 57.41; H 5.13: F 2.93%: Found: C 57.77; H 5.28; F 3.21%

(2) 7-O-(2,6-dideoxy-2-fluoro-α-L-talopyranosyl) daunomycinone

7-O-(2,6-dideoxy-2-fluoro-2-fluoro-α-L-talopyranosyl) daunomycinone (100 mg) obtained as above was dissolved in 0.2N aqueous sodium hydroxide solution (8 ml), and the solution was allowed to cause hydrolysis at 0° C. for 5 hours, whereby to remove the acetyl groups. The reaction solution obtained was neutralized at that temperature with the addition of 1N hydrochloric acid (1.6 ml), after which sodium chloride (1.5 g) was added thereto, and the mixture was extracted with chloroform. The extract in chloroform was washed with a saturated aqueous sodium chloride solution and then concentrated. The red solid residue obtained was repreciptated form a mixture of chloroform and hexane to yield the titled compound as a red solid (62 mg; 72%).

$[\alpha]_D^{25} +197°$ (c 0.02, chloroform-methanol=1:1)

$^1$H-NMR spectrum (deuteropyridine): $\delta 6.02$ (1H, broad d, H-1') 3.98 (3H, s, OCH$_3$) $\delta 2.57$ (3H, s, Acetyl)

EXAMPLE 6

Production of 7-O-(2,6-dideoxy-2-fluoro-α-L-talopyranosyl)adriamycinone

7-O-(2,6-dideoxy-2-fluoro-α-L-talopyranosyl) daunomycinone (37.8 mg) prepared as in Example 5 was suspended in a mixture of dry methanol (0.9 ml) and dry dioxane (1.4 ml). Then, methyl orthoformate (0.052 ml) was added to the resultant suspension for the reaction to protect the 13-carbonyl group of the daunomycinone derivative by ketalization into the form of the dimethylketal. Thereafter, the resulting reaction mixture was cooled to 0°C., followed by adding to the suspension a solution of bromine (15 mg) in dry dichloromethane (0.15 ml). The resulting mixture was stirred at 0° C. for 1 hour and then at room temperature for 1.5 hours, whereby to brominate the methyl group at the 14-position of the daunomycinone derivative.

The resulting homogeneous solution was added dropwise to isopropyleter (12 ml), and red precipitate thus formed was recovered by centrifuging and washed twice with isopropyleter. The precipitate was then suspended in acetone (3 ml) and the suspension was stirred at room temperature for 40 minutes to conduct the deketalization reaction. Concurrently, the acetone reacted with the daunomycinone derivative to give the 3', 4'-O-isopropylidene derivative therefrom. To the homogenous solution thus formed were added isopropyleter (5 ml) and hexane (20 ml), and the precipitate deposited was recovered by centrifuging to afford a red solid (35 mg) mainly comprising 7-O-(2,6-dideoxy-2-fluoro-3,4-O-isopropylidene-α-L-talopyranosyl)-14-bromodaunomycinone. The red solid obtained was dissolved in a mixture of acetone (3.2 ml) and water (0.8 ml), to which sodium formate (65 mg) was added. The mixture obtained was vigorously stirred at room temperature for 17 hours, whereby to convert the bromo group at the 14-position of the danomycinone derivative into the hydroxyl group, occasionally together with the formyloxy group. The reaction solution obtained was concentrated to a small volume and the side thus deposited was washed with water and dried to afford a red solid (29 mg). This solid was dissolved in chloroform-methanol (1:1, 3 ml) containing aqueous 1M ammonia (0.37 ml) and was kept at 0° C. for 40 minutes (the formyl group as by-formed was removed by this procedure). After concentration, the residue was dissolved in a 80% aqueous acetic acid (1.4 ml), and the solution thus formed was heated at 80° C. for 1.5 hours. This heating served to remove the 3',4'-O-isopropylidene group which had been introduced by the acetone treatment as above. The reaction solution so obtained was concentrated in vacuo, and water was added to the residue. The resulting mixture was centrifuged to collect the solid material which was then washed with water. The solid material so obtained was reprecipitated from a mixture of chloroform, methanol and isopropyleter (5:1:40 by volume) to afford the titled compound as a red solid (16.7 mg; Yield 43%). The water washings above were passed through a column of 3 ml of Diaion HP-50 resin (Diaion is a registered trade mark of a microporous, adsorbent resin as produced by Mitsubishi Chemical Industries, Ltd.). The resin column was washed with water and then eluted with aqueous 80% methanol, namely a mixture of methanol and water (4:1 by volume). Fractions containing the titled compound (fraction Nos. 3-21 fraction, 15-105 ml) were collected, combined together and concentrated to afford a second crop (5 mg) of the titled compound as a red solid. The total yield of the desired compound was 21.7 mg (56%).

$[\alpha]_D^{25} +194°$ (c 0.01, chloroform-methanol (1:1 by volume)) $^1$H-NMR spectrum (pyridine-d$_5$): δ5.95 (1H, broad d, H-1') 5.33 (2H, s, CH$_2$OH) 3.96 (3H, s, OCH$_3$)

What we claim is:

1. A process for the production of methyl 2,6-dideoxy-2-fluoro-α-L-talopyranoside of the formula

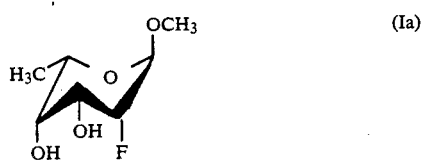

which comprises the steps of:
(a) reacting potassium hydrogen fluoride or sodium hydrogen fluoride with a methyl 2,3-anhydro-4-O-protected-6-deoxy-α-L-gulopyranoside of the formula

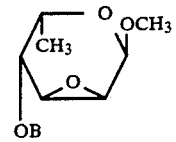

wherein B is a hydroxyl-protecting benzyl or acetyl group, in solution in an organic solvent selected from the group consisting of lower alkylene glycols and 2,3-dihydroxylbutane, at a temperature of 100° to 250° C.; the amount of potassium or sodium hydrogen fluoride used being in a proportion of 5 to 30 mol per mol of the compound of the formula (II), whereby there is preferentially produced a methyl 4-O-protected-2,6-dideoxy-2-fluoro-α-L-idopyranoside of the formula

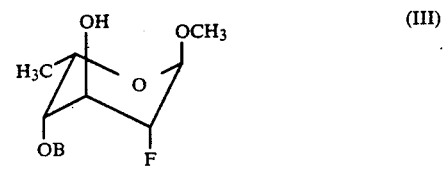

wherein B is as defined above,
(b) reacting the compound of the formula (III) with an oxidizing agent selected from the group consisting of dimethylsulfoxide and pyridinium chlorochromate, in solution in dimethylsulfoxide or a mixture of benzene with dimethylsulfoxide, at room temperature, to produce a methyl 4-O-protected-2,6-dideoxy-2-fluoro-α-L-lyxo-hexopyranosid-3-ulose of the formula

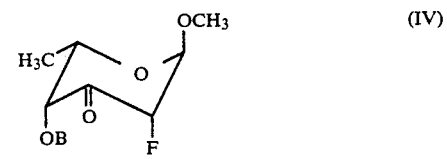

wherein B is as defined above,
(c) reacting the compound of the formula (IV) with a metal hydride as the reducing agent in solution in a reaction medium comprising tetrahydrofuran, ethyl ether or diglyme, at a temperature of minus 30° C. to plus 30° C., to produce a methyl 4-O-protected-2,6-dideoxy-2-fluoro-α-L-talopyranoside of the formula

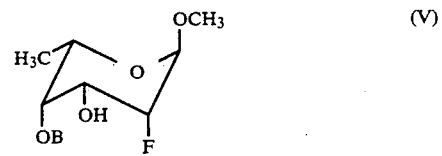

wherein B is as defined above, and
(d) removing the hydroxyl-protecting group (B) from the compound of the formula (V) to produce the compound of the formula (Ia).

* * * * *